(12) United States Patent
Johnson

(10) Patent No.: US 10,952,808 B2
(45) Date of Patent: Mar. 23, 2021

(54) PLANAR ILLUMINATOR FOR OPHTHALMIC SURGERY

(71) Applicant: NOVARTIS AG, Basel (CH)

(72) Inventor: Andrew David Johnson, Laguna Niguel, CA (US)

(73) Assignee: Alcon, Inc., Fribourg (CH)

( * ) Notice: Subject to any disclaimer, the term of this patent is extended or adjusted under 35 U.S.C. 154(b) by 559 days.

(21) Appl. No.: 15/683,090

(22) Filed: Aug. 22, 2017

(65) Prior Publication Data

US 2018/0055596 A1 Mar. 1, 2018

Related U.S. Application Data

(60) Provisional application No. 62/379,365, filed on Aug. 25, 2016.

(51) Int. Cl.
*A61B 1/07* (2006.01)
*A61B 3/10* (2006.01)
(Continued)

(52) U.S. Cl.
CPC ............. *A61B 90/30* (2016.02); *A61B 1/002* (2013.01); *A61B 1/00167* (2013.01); *A61B 1/07* (2013.01);
(Continued)

(58) Field of Classification Search
CPC ............. A61B 90/30; A61B 2090/306; A61B 1/00167; A61B 1/0017; A61B 1/002; A61B 1/07; A61B 3/00; A61B 3/0008; A61B 1/00165; A61B 1/00163; A61B 3/12–14; A61B 1/0669; A61B 1/06; A61B 1/0661; A61B 1/0646; A61F 9/007; A61F 9/0079; A61F 9/008; A61F 2009/00861; A61F 2009/00863; A61F 2009/00865; A61F 2009/00868; A61F 2009/0087; A61F 2009/00872; A61F 2009/00874; A61F 2009/00876; A61F 2090/00861; A61F 2090/00863; A61F 2090/00865; A61F 2090/00868; A61F 2090/0087; A61F 2090/00872; A61F 2090/00874; A61F 2090/00876; A61N 5/062;
(Continued)

(56) References Cited

U.S. PATENT DOCUMENTS 4,964,692 A 10/1990 Prescott
5,201,730 A 4/1993 Easley et al.
(Continued)

FOREIGN PATENT DOCUMENTS

CN 101299972 A 11/2008
CN 102740780 A 10/2012
(Continued)

*Primary Examiner* — Ryan N Henderson
*Assistant Examiner* — Pamela F Wu

(57) ABSTRACT

The present disclosure provides illumination apparatus for ophthalmic surgery comprising a light that provides planar field illumination, as well as methods of using the illumination apparatus. The illuminators of the present disclosure can be used in intraocular refractive and vitroretinal surgery to better enable visualization of anatomical structures of the eye currently difficult to view, capturing detail that would normally be obscured using conventional illumination apparatus.

16 Claims, 9 Drawing Sheets

(51) Int. Cl.
*A61B 90/30* (2016.01)
*A61B 3/00* (2006.01)
*A61F 9/007* (2006.01)
*A61B 1/00* (2006.01)
*A61B 1/002* (2006.01)
*F21V 8/00* (2006.01)
*A61B 1/005* (2006.01)
*A61B 3/13* (2006.01)
*A61F 9/008* (2006.01)
*A61N 5/06* (2006.01)

(52) U.S. Cl.
CPC ............ *A61B 3/0008* (2013.01); *A61F 9/007* (2013.01); *A61B 1/0057* (2013.01); *A61B 3/13* (2013.01); *A61B 2090/306* (2016.02); *A61F 9/008* (2013.01); *A61F 9/00821* (2013.01); *A61F 2009/00863* (2013.01); *A61F 2009/00874* (2013.01); *A61N 2005/063* (2013.01); *G02B 6/0008* (2013.01)

(58) Field of Classification Search
CPC ............ A61N 2005/063; G02B 6/0008; G02B 6/001; G02B 6/0011; G02B 6/0013; G02B 6/0023; G02B 6/0025; G02B 6/0026; G02B 6/0028; G02B 6/003; G02B 6/0033; G02B 6/0035; G02B 6/005; G02B 6/0005; G02B 6/0015–6/0016; G02B 6/0018; G02B 6/002; G02B 21/0032
USPC ................ 600/182, 178, 179, 160, 164–166
See application file for complete search history.

(56) References Cited

U.S. PATENT DOCUMENTS

| | | | |
|---|---|---|---|
| 5,275,593 A | 1/1994 | Easley et al. | |
| 5,591,160 A | 1/1997 | Reynard | |
| 5,630,809 A | 5/1997 | Connor | |
| 5,651,783 A | 7/1997 | Reynard | |
| 5,798,840 A | 8/1998 | Beiting | |
| 7,731,710 B2 | 6/2010 | Smith | |
| 7,783,346 B2 | 8/2010 | Smith et al. | |
| 8,152,798 B2 | 4/2012 | Smith | |
| 8,292,434 B2 | 10/2012 | Horvath et al. | |
| 8,317,689 B1* | 11/2012 | Remijan | A61B 1/00142 600/112 |
| 8,358,463 B2 | 1/2013 | Jaw | |
| 8,480,279 B2 | 7/2013 | Papac et al. | |
| 8,485,972 B2 | 7/2013 | Papac et al. | |
| 8,968,347 B2* | 3/2015 | McCollam | A61B 90/30 606/170 |
| 8,993,984 B2 | 3/2015 | Gord | |
| 9,055,885 B2 | 6/2015 | Horvath et al. | |
| 9,089,364 B2 | 7/2015 | Bhadri et al. | |
| 9,364,982 B2 | 6/2016 | Schaller | |
| 9,402,643 B2 | 8/2016 | Auld et al. | |
| 9,561,085 B2 | 2/2017 | Yadlowsky et al. | |
| 9,839,749 B2 | 12/2017 | Johnson et al. | |
| 9,956,053 B2 | 5/2018 | Diao et al. | |
| 10,016,248 B2 | 7/2018 | Mirsepassi et al. | |
| 10,039,669 B2 | 8/2018 | Heeren | |
| 2009/0161384 A1 | 6/2009 | Smith | |
| 2012/0050684 A1* | 3/2012 | Smith | A61B 3/0008 351/221 |
| 2012/0147329 A1* | 6/2012 | Papac | A61B 90/30 351/213 |
| 2013/0038836 A1 | 2/2013 | Smith | |
| 2014/0121469 A1 | 5/2014 | Meekel et al. | |
| 2014/0288417 A1 | 9/2014 | Schmidtlin et al. | |
| 2015/0196193 A1* | 7/2015 | Kienzle | A61B 1/015 600/109 |
| 2015/0196199 A1* | 7/2015 | Toda | A61B 3/1216 351/206 |
| 2015/0223976 A1* | 8/2015 | Bouch | A61B 90/30 606/4 |
| 2016/0066777 A1 | 3/2016 | Peterson | |
| 2017/0014023 A1 | 1/2017 | Kern | |
| 2017/0014267 A1 | 1/2017 | Kern et al. | |
| 2017/0119491 A1 | 5/2017 | Mirsepassi et al. | |
| 2017/0165114 A1 | 6/2017 | Hallen et al. | |
| 2018/0055596 A1 | 3/2018 | Johnson | |
| 2018/0132963 A1 | 5/2018 | Diao et al. | |
| 2018/0133057 A1 | 5/2018 | Diao et al. | |
| 2018/0140373 A1 | 5/2018 | Dos Santos | |
| 2018/0168768 A1 | 6/2018 | Mirsepassi et al. | |
| 2018/0168861 A1 | 6/2018 | Mirsepassi et al. | |
| 2018/0338776 A1 | 11/2018 | Farley et al. | |
| 2018/0338859 A1 | 11/2018 | Mirsepassi et al. | |
| 2018/0338860 A1 | 11/2018 | Farley | |

FOREIGN PATENT DOCUMENTS

| | | |
|---|---|---|
| GB | 2480440 A | 11/2011 |
| JP | 2008086780 A | 4/2008 |
| JP | 2014512223 A | 5/2014 |
| JP | 2014527430 A | 10/2014 |

\* cited by examiner

PLANAR ILLUMINATOR FOR OPHTHALMIC SURGERY

FIELD

The present disclosure relates to ophthalmic illuminators. More particularly, the present disclosure relates to devices, systems, and methods for providing planar illumination during ophthalmic surgery.

BACKGROUND

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Ophthalmic microsurgical procedures can require precision cutting and/or removing of various body tissues of the patient's eye. For example, during a surgical procedure, a user, such as a surgeon or other medical professional, may hold an illumination apparatus in one hand and a vitrectomy probe in his or her other hand. The vitrectomy probe can be used to perform surgical maneuvers while the surgeon visualizes the patient's eye using the light provided by the illumination apparatus. The illumination apparatus may include a cannula inserted into the eye and one or more optical fibers encompassed within the center cavity of the cannula. Because illumination apparatus typically transmit wide-angle light that illuminates a volume of space within the eye, details of anatomical structures of the eye may be obscured due to contribution from scattered light in front and behind of features of interest.

Accordingly, there remains a need for improved devices, systems, and methods that allow a surgeon to illuminate a patient's eye with a planar light beam or laser sheet that illuminates a planar slice or field of an anatomical feature rather than a volume of space.

SUMMARY

This summary is provided to introduce a selection of concepts in a simplified form that are further described below and in the attendant drawings. This summary is not intended to identify key or essential features of the claimed subject matter, nor is it intended to be used to limit the scope of the claimed subject matter. Other features, details, utilities, and advantages of the claimed subject matter will be apparent from the following written detailed description, including those aspects illustrated in the accompanying drawings and defined in the appended claims.

The present disclosure addresses an unmet medical need by, among other things, uniquely outputting a planar light beam into a patient's eye during an ophthalmic surgical procedure such as, e.g., a vitrectomy. An illumination apparatus may include multiple optical fibers positioned within a cannula. The cannula is inserted into the patient's eye. The optical fibers can be sized and shaped to respectively transmit light having different illumination profiles. For example, one optical fiber may transmit light for wide-field volumetric illumination to provide general situational awareness for a surgeon during the surgical procedure. A second optical fiber device may transmit light for a planar field illumination. Planar field illumination may allow the surgeon to better visualize anatomy within the patient's eye, such as vitreous humor. For example, during vitrectomy, visualizing the vitreous and its interaction with the retina can be difficult since it is a naturally optically clear medium. An optical fiber device that illuminates a planar field in the eye may enhance visualization of the vitreous by isolating light from a single plane in the viewing path. With such an illumination apparatus, a surgeon can toggle between multiple illumination profiles—i.e., volumetric illumination or planar field illumination—depending the surgeon's visualization needs during the surgical procedure.

Thus, in some embodiments the present disclosure provides an ophthalmic illumination apparatus comprising a body sized and shaped for grasping by a user; a cannula coupled to the body and configured to be positioned within an eye of a patient; an optical fiber disposed within the cannula, where the optical fiber is configured to transmit light having a volumetric illumination profile; and an optical fiber device disposed within the cannula, wherein the optical fiber device is configured to transmit light having a planar illumination profile.

In some aspects of such these embodiments, the optical fiber device comprises one of an optical slit, a rod lens or a ball lens. In another aspect, at least one of the optical fiber or the optical fiber device is translatable with respect to the cannula. Further, aspects may additionally include an input device configured to receive a user input to cause one of the optical fiber or the optical fiber device to selectively illuminate the eye of the patient; a light source coupled to the optical fiber and the optical fiber device and configured to output light to selectively illuminate the eye of the patient via the optical fiber or the optical fiber device; an optical relay disposed between a light source and the cannula, where the optical relay is configured to selectively direct the light output by the light source to one of the optical fiber or the optical fiber device in response to the user input; a third optical fiber disposed within the cannula where the third optical fiber is coupled to a therapeutic light source and configured to transmit a therapeutic light beam into the eye of the patient; an endoscopic fiber bundle disposed within the cannula and configured to visualize the eye the patient; and/or a deflection mechanism coupled to the cannula and configured to selectively bend the cannula.

Other embodiments described in the disclosure provide an optical fiber device comprising an optical fiber device housing; an optical fiber comprising a core and cladding axially disposed within the optical fiber device housing; and one or more of an optical slit device, a rod lens, and a ball lens coupled to the optical fiber device housing.

Some aspects of these embodiments comprise one or more of an optical slit device comprising an optical slit disposed within an optical end cap coupled to a distal end of the optical fiber device housing, a rod lens positioned perpendicularly to the optical fiber and coupled to a distal end of the optical fiber device housing, and a ball lens disposed within a distal end of the optical fiber device housing.

Yet other embodiments described include methods for ophthalmic surgical illumination comprising illuminating an eye of a patient with light having a volumetric profile, where the light having the volumetric profile is transmitted by an optical fiber disposed within a cannula positioned within the eye; and illuminating the eye of the patient with light having a planar profile, where the light having the planar profile is transmitted by an optical fiber device disposed within the cannula.

Aspects of these embodiments may also include receiving user input at an input device to cause a light source coupled to an optical fiber and an optical fiber device to output light to one of the optical fiber or the optical fiber device.; an optical relay disposed between a light source and the cannula that selectively directs the light output by the light source to one of the optical fiber or the optical fiber device, and/or receiving a user input at an input device to cause one of the first light source coupled to the optical fiber or the second light source coupled to the optical fiber device to selectively output light to illuminate the eye of the patient.

These and other aspects and uses will be described in the detailed description.

BRIEF DESCRIPTION OF THE FIGURES

FIG. 6A shows illumination from a prior art optical fiber providing wide-field volumetric illumination. FIG. 6B shows illumination from an optical fiber device as described herein that emits a planar light beam.

Figure 1:
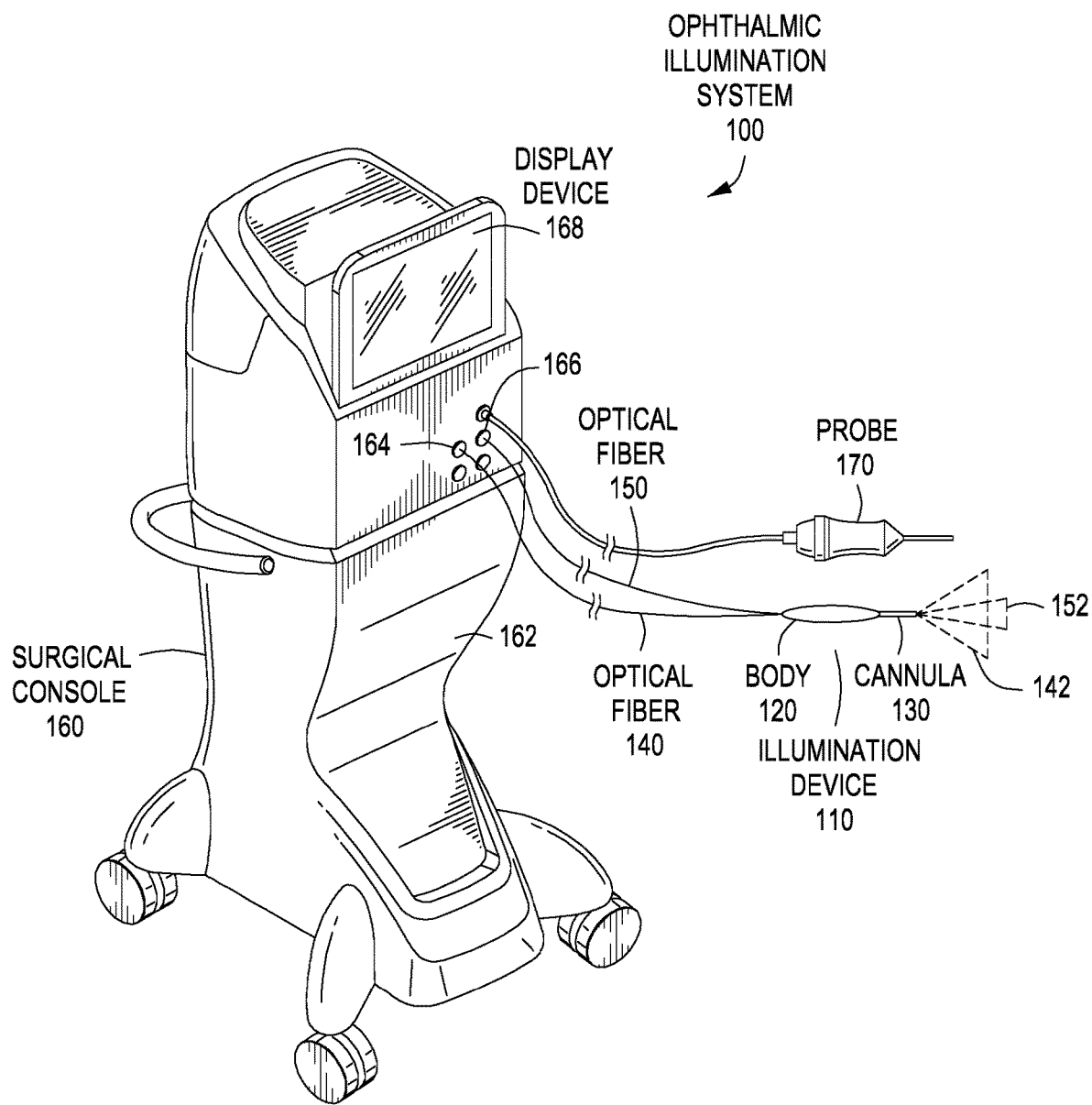
FIG. 1 is an illustration of an embodiment of an ophthalmic illumination system.

In the drawings, elements having the same designation have the same or similar functions. Those skilled in the art will appreciate that FIGS. 1-8 are not necessarily to scale, and that several of the features may be exaggerated to more clearly illustrate various features. Those skilled in the art will also appreciate that the illustrated structures are exemplary only, and not limiting.

DETAILED DESCRIPTION

Before the present optical fiber devices capable of illuminating a planar field within the eye and systems incorporating such optical fiber devices are described, it is to be understood that this disclosure is not limited to the specific embodiments described, as such may vary. It is also to be understood that the terminology used herein is for the purpose of describing particular aspects only and is not intended to limit the scope of the present disclosure.

Note that as used in the present specification and in the appended claims, the singular forms "a," "an," and "the" include plural referents unless the context clearly dictates otherwise.

Unless defined otherwise, all technical and scientific terms used herein have the same meaning as commonly understood by one of ordinary skill in the art to which this disclosure belongs. Any publications mentioned herein are incorporated herein by reference for the purpose of describing and disclosing devices and methodologies that are described in the reference and which might be used in connection with this disclosure.

Where a range of values is provided, it is understood that each intervening value between the upper and lower limit of that range and any other stated or intervening value in that stated range is included as an embodiment of the disclosure. The upper and lower limits of these smaller ranges are also included as an embodiment of the disclosure, subject to any specifically excluded limit in the stated range. Where the stated range includes both the upper and lower limits, ranges excluding either of those included limits are also included as an embodiment of the disclosure.

In the following description, numerous specific details are set forth to provide a more thorough understanding of the present disclosure. However, it will be apparent to one of skill in the art upon reading the specification that the present disclosure may be practiced without one or more of these specific details. In other instances, features and procedures to well-known to those skilled in the art have not been described in order to avoid obscuring the disclosure.

The present disclosure describes devices, systems, and methods of selectively illuminating a planar field in a patient's eye. In certain embodiments, two or more optical fibers, optical fiber devices, or combinations thereof can be positioned within a cannula of an ophthalmic illumination apparatus. The cannula can be inserted into the patient's eye. The optical fibers can be differently sized, shaped, and/or configured with lenses, optical slits, or other structures such that they emit light having different field illumination profiles. The surgeon can choose which optical fiber or optical fiber device emits light during the surgical procedure depending on the desired field illumination; that is, the surgeon can select a, e.g., wide field illumination of a volume within the eye, or a focused illumination of a specific plane within the eye. Further, the cannula in some embodiments can be deflected such that a desired area, such as the periphery of the eye, can be illuminated. In addition, in some embodiments an optical fiber transmitting a therapeutic laser beam and and/or endoscopy fiber bundle can also be positioned within the cannula of the illumination apparatus.

The devices, systems, and methods of the present disclosure provide numerous advantages, including: (1) increased control of intra-operative illumination for the surgeon; (2) improved operating conditions for the surgeon with the ability to adjust retinal glare; (3) decreased risk of phototoxicity for the patient; (4) enhanced visualization of anatomy, such as the vitreous humor, for the surgeon using planar field illumination while preserving situational awareness for the surgeon using, e.g., wide-angle volumetric illumination; (5) increased illumination area within the patient's eye with cannula deflection; and (6) improved working conditions for the surgeon with incorporation of multiple fibers for illumination, treatment, and/or endoscopy into a single apparatus.

Figure 2:
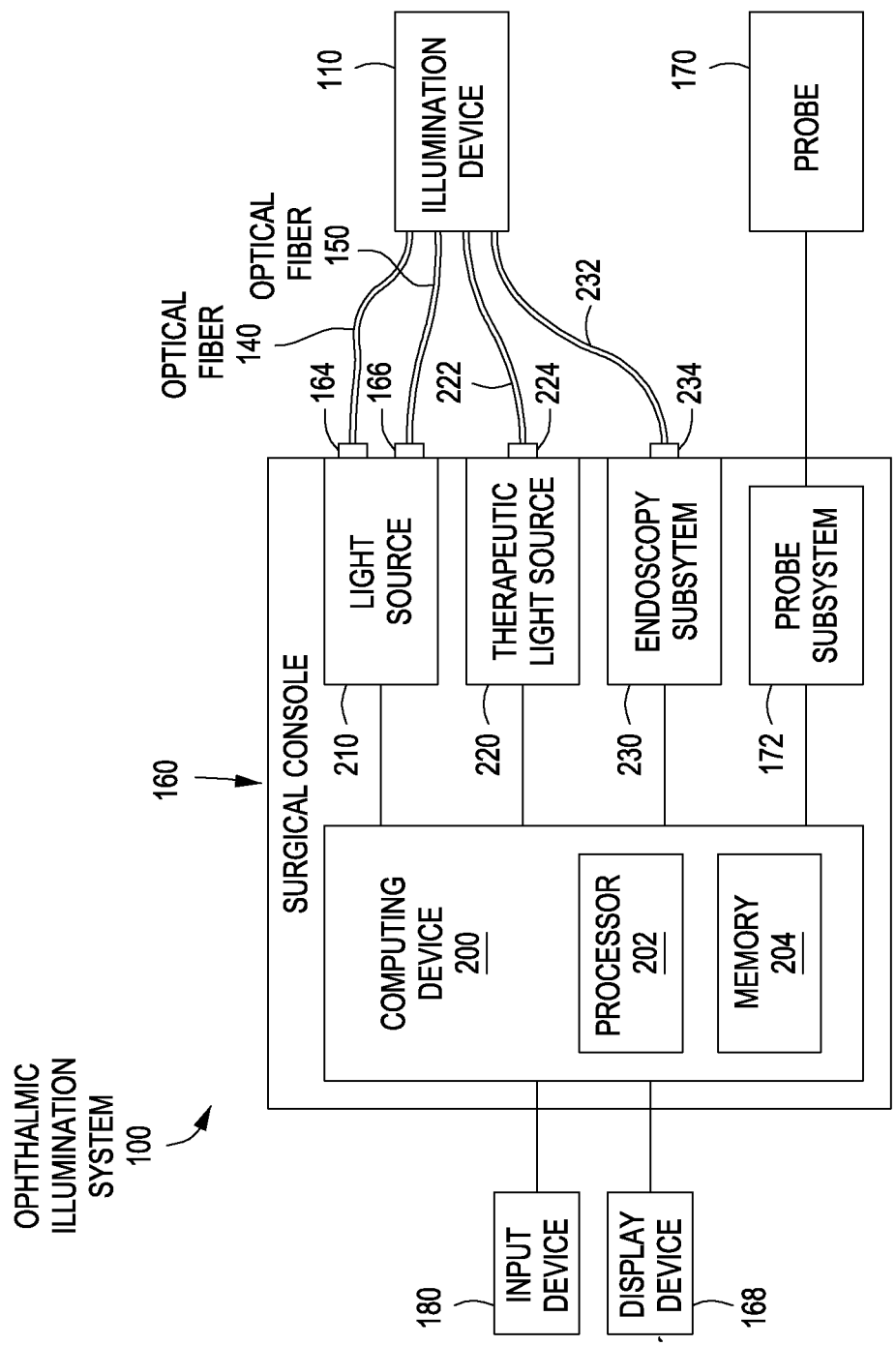
FIG. 2 is a schematic diagram illustrating an embodiment of an ophthalmic illumination system.
Figure 3:
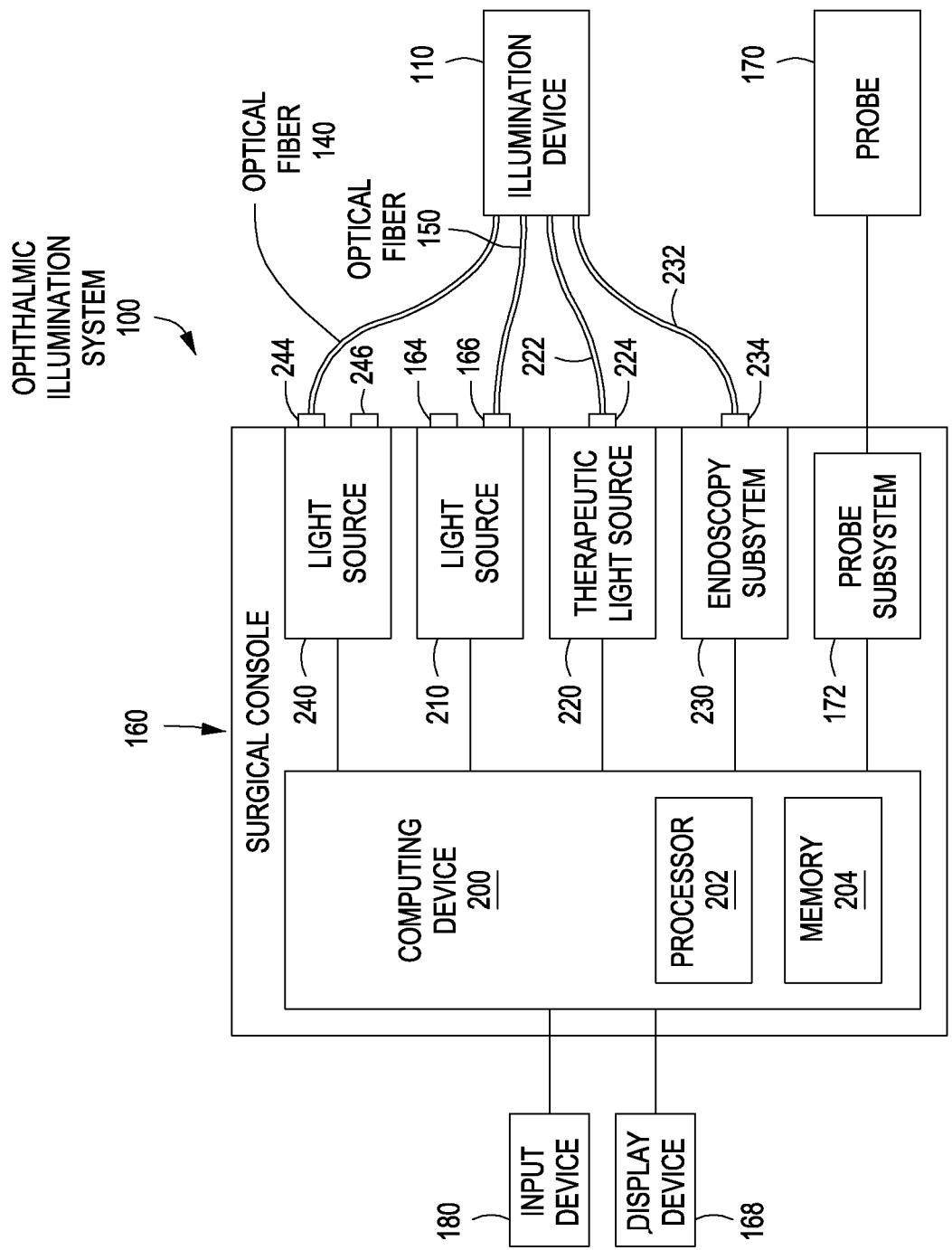
FIG. 3 is a schematic diagram illustrating an embodiment of an ophthalmic illumination system.
Figure 4:
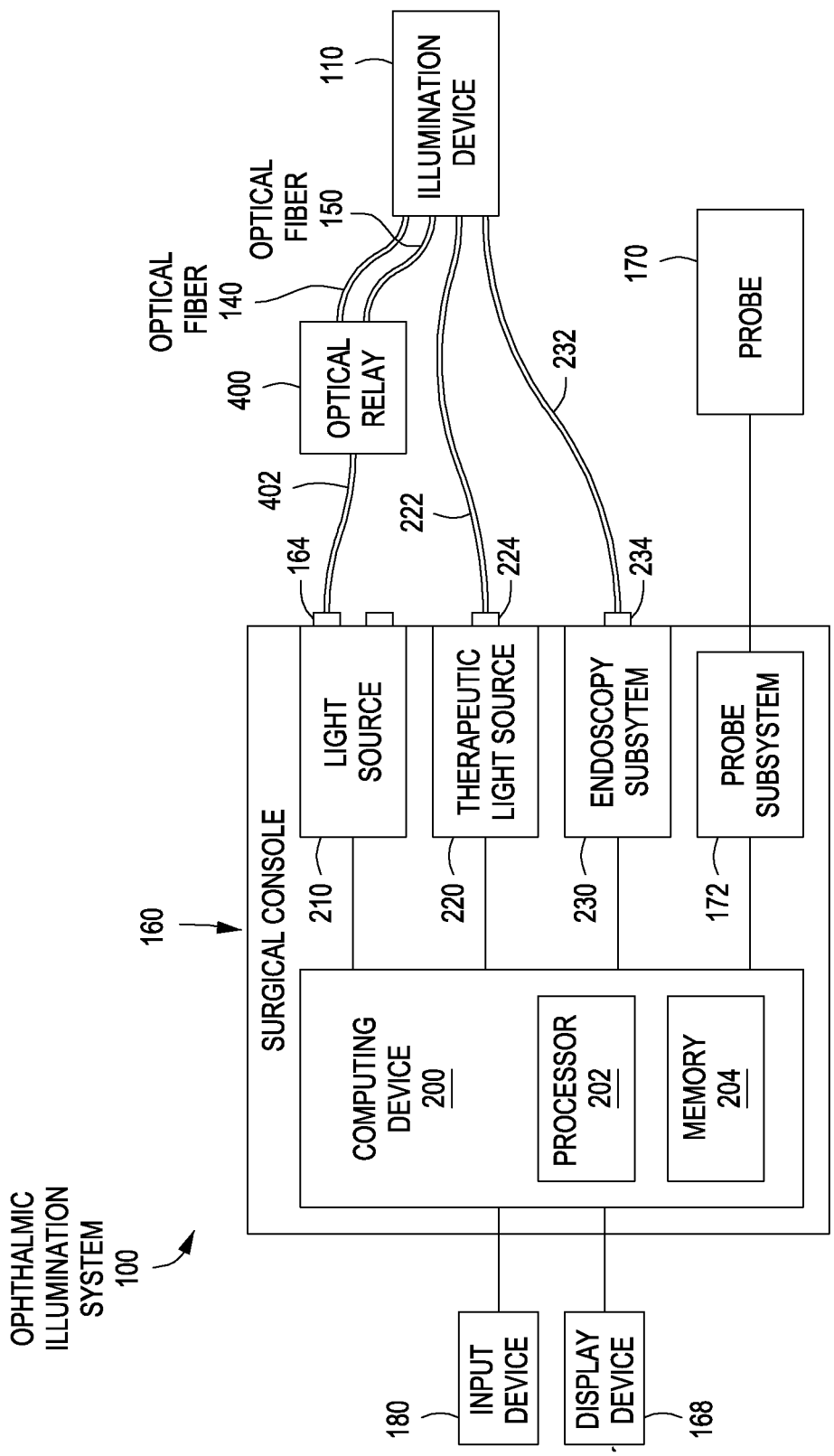
FIG. 4 is a schematic diagram illustrating an embodiment of an ophthalmic illumination system.

FIGS. 1, 2, 3, and 4 illustrate exemplary ophthalmic illumination systems 100. FIG. 1 is an exemplary illustration of an ophthalmic illumination system 100. FIGS. 2, 3, and 4 are various exemplary embodiments of schematic diagrams of the ophthalmic illumination system 100. The ophthalmic illumination system 100 can include an illumination apparatus 110 having a body 120 and a cannula 130. Body 120 can be sized and shaped for grasping by a user, and cannula 130 is coupled to the body, either directly or indirectly. Cannula 130 is configured to be positioned within a surgical field, such as a patient's eye. Illumination apparatus 110 in this embodiment includes optical fiber 140 and optical fiber device 150 disposed within cannula 130. Optical fiber 140 can be configured to transmit light 142 having a volumetric field profile, and optical fiber device 150 can be configured to transmit light 152 having a planar field profile. Optical fiber 140 and optical fiber device 150 thus are configured to selectively illuminate different fields within the patient's eye.

The ophthalmic illumination system 100 can be used to perform various ophthalmic surgical procedures including an anterior segment procedure, a posterior segment procedure, a vitreoretinal procedure, a vitrectomy procedure, a cataract procedure, and/or other desired procedures. The user, such as a surgeon or other medical professional, operates the illumination apparatus 110 to illuminate the surgical field. The surgical field may include any suitable physiology of the patient's eye, including an anterior segment, a posterior segment, a cornea, a lens, a vitreous chamber, transparent membranes, blood vessels, a retina, a macula, a foveola, a fovea centraalis, a para fovea, a perifovea, an optic disc, an optic cup, and/or other biological tissue.

Figure 7:
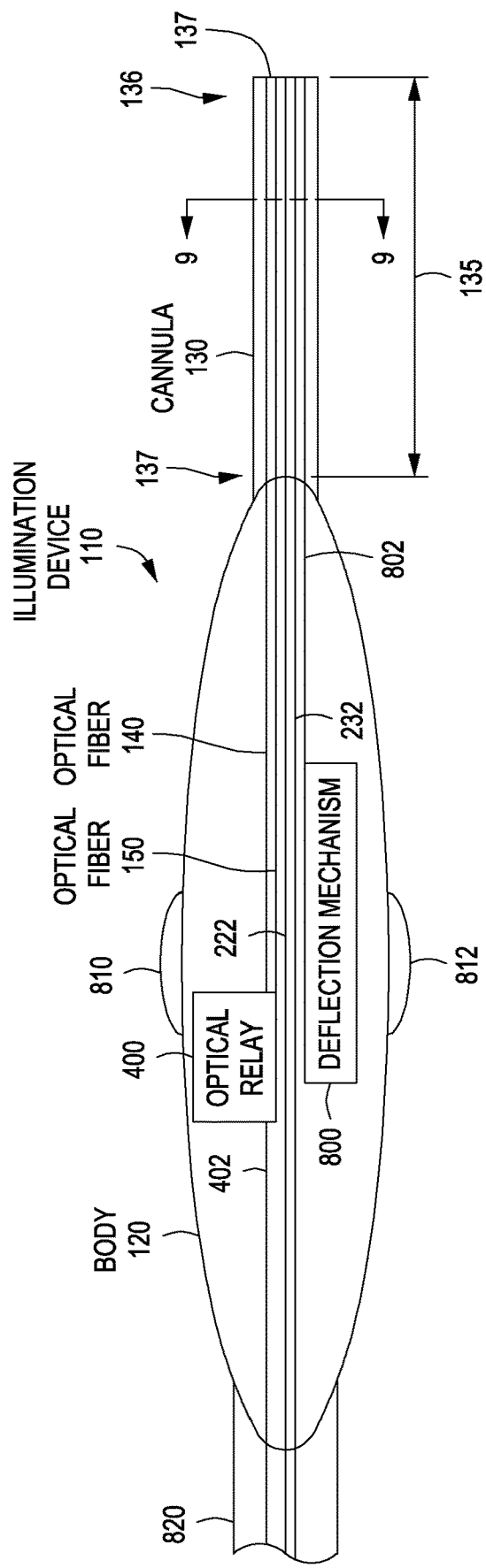
FIG. 7 is an illustration of an embodiment of a cross-sectional longitudinal view of an illumination apparatus.

Referring to FIGS. 1 and 7, body 120 of the illumination apparatus 110 can form a handle for the illumination apparatus 110. FIG. 7 represents an exemplary longitudinal cross-sectional, side-view illustration of the illumination apparatus 110. Body 120 can be sized and shaped for handheld use and/or grasping by the user. For example, body 120 can be any suitable shape, including ellipsoidal, polygonal, tubular, other desired shapes, and/or combinations thereof. Body 120 can be made of any suitable material, such as a thermoplastic or metal, and can be formed by any method, including, for example, injection molding or machining. Further, in some embodiments, at least a portion of body 120 may be knurled, patterned, and/or otherwise textured to improve gripping. Body 120 may be formed of two or more sections joined together, and can include one, two, three, or more controls 810, 812. Controls 810, 812 can be buttons, sliders, toggles, wheels, other suitable actuatable components, and/or combinations thereof, and are used to control various functions of the illumination apparatus 110 as described herein. In that regard, controls 810, 812 can be an input device 180 as further described herein.

Figure 5A:
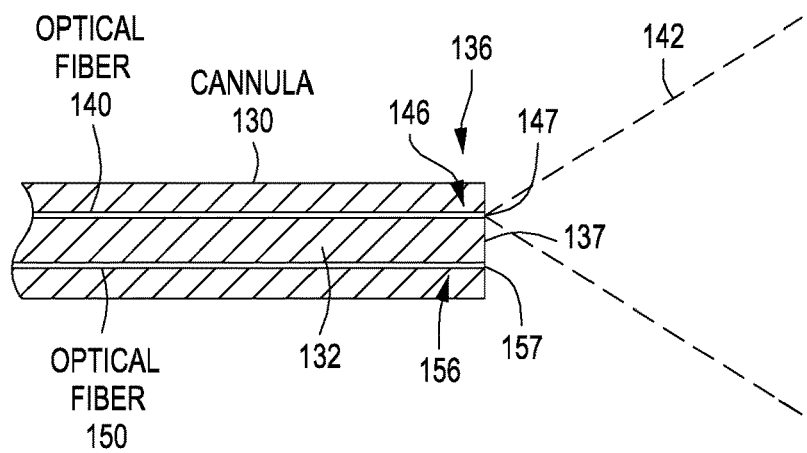
FIGS. 5A, 5B, and 5C are illustrations of various embodiments of an a cannula of an illumination apparatus comprising both an optical fiber that illuminates a volumetric field within the eye and an optical fiber device that illuminates a planar field within the eye.
Figure 5B:
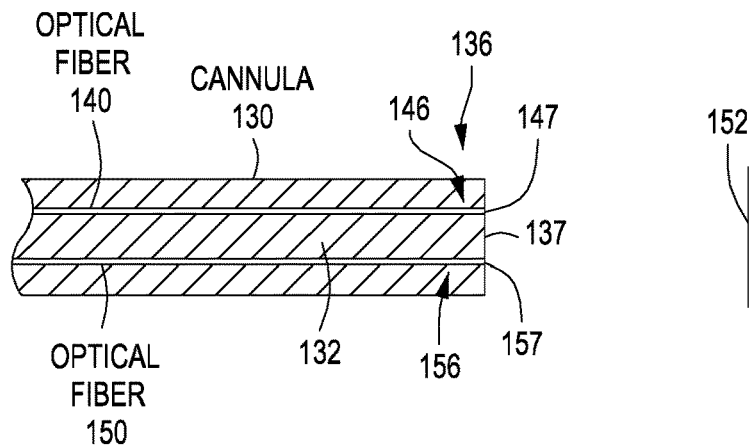
Figure 5C:
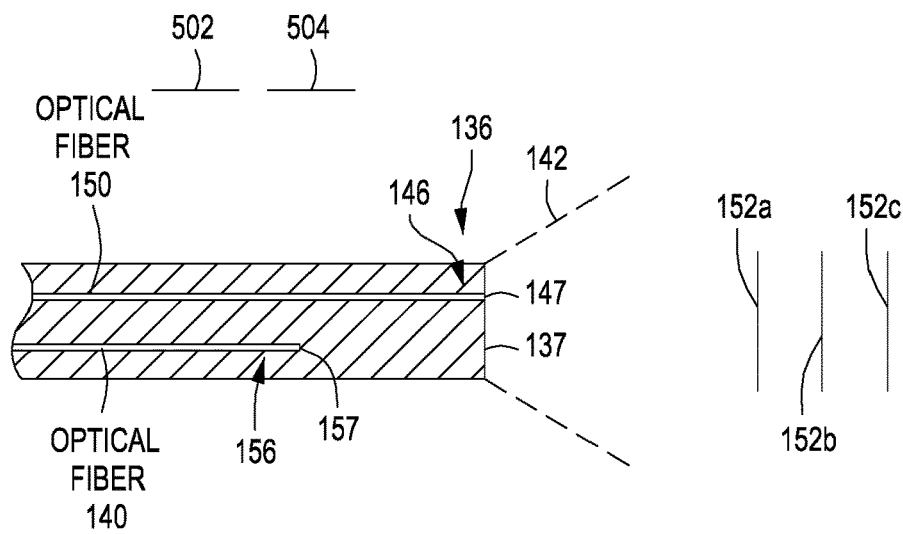
Figure 8:
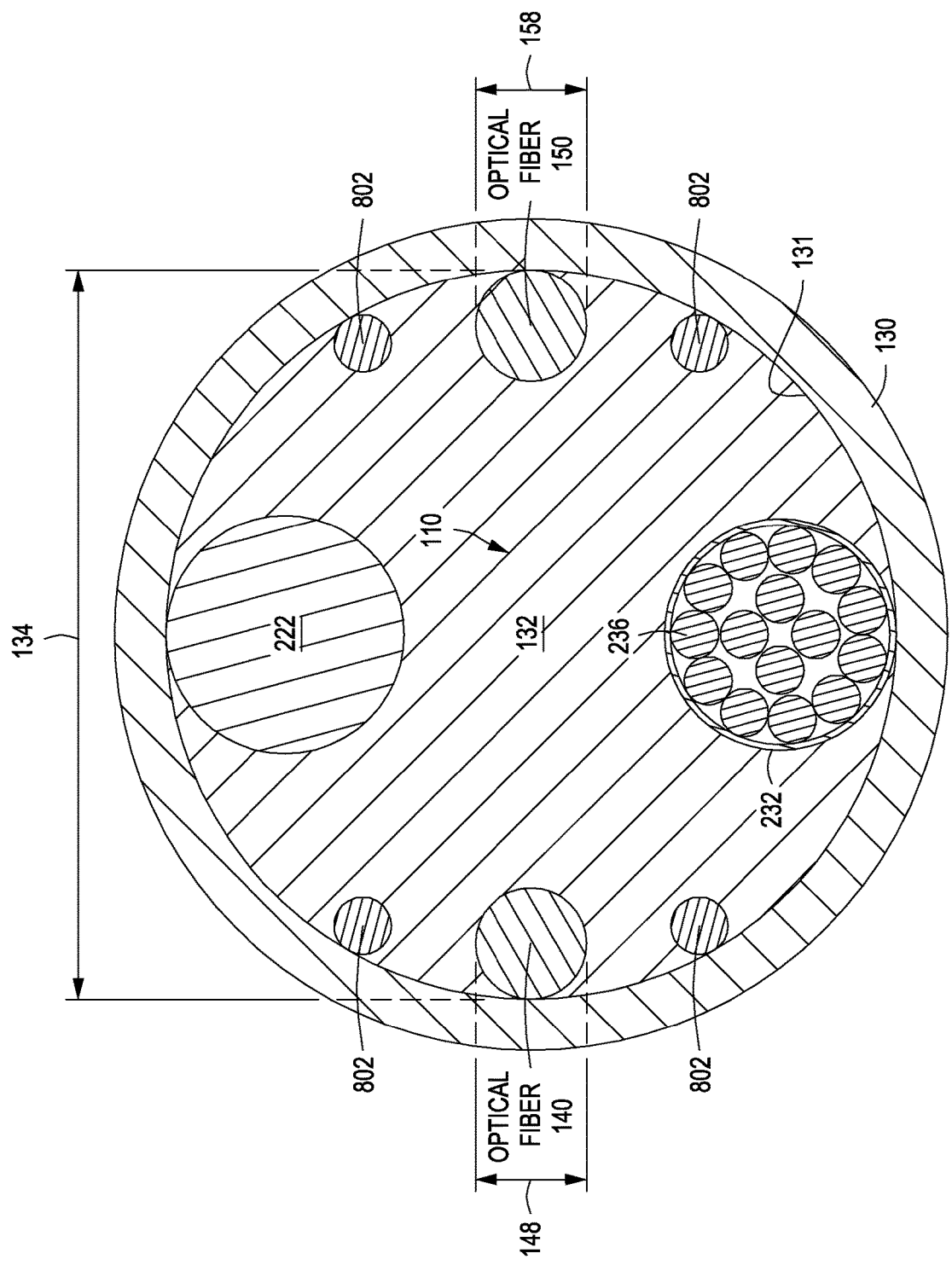
FIG. 8 is an embodiment of a cross-sectional end view illustration of a cannula of an illumination apparatus.

Referring to FIGS. 1, 5A, 5B, 5C, 7, and 8, cannula 130 of the illumination apparatus 110 can extend from body 120. FIGS. 5A, 5B, and 5C represent exemplary cross-sectional, side-view illustrations of cannula 130. FIG. 8 is an exemplary cross-sectional, end view of cannula 130 taken along section line 9-9 of FIG. 7. Cannula 130 can include a lumen 132, a distal portion 136, and a proximal portion 137. In this embodiment, cannula 130 is directly coupled to body 120 at proximal portion 137. Cannula 130, including distal portion 136, can be sized and shaped for insertion into an interior space of the eye, such as the vitreous chamber. Cannula 130 can be any suitable material, including medical grade tubing; a metal, such as titanium, stainless steel; or a suitable polymer. Cannula 130 can be any desired size, including 16-27 Gauge tubing, and/or other suitable sizes, both larger and smaller. Cannula 130 can have an internal diameter 134 and a length 135. The internal diameter 134 can be between approximately 400 microns and approximately 600 microns, between approximately 400 microns and approximately 550 microns, between approximately 400 microns and approximately 500 microns, and/or other suitable sizes, both larger and smaller. The length 135 of cannula 130 can be between approximately 20 mm and approximately 50 mm, between approximately 20 mm and approximately 40 mm and/or other suitable sizes, both larger and smaller. Cannula 130 can have a cross-section shaped as a polygon, an ellipse, other suitable shape, and/or a combination thereof. For example, cannula 130 can be cylindrically-shaped so as to have a circular cross-section.

Any of the illumination apparatus 110, body 120, and/or cannula 130 can be disposable or configured for a single use. Alternatively, any of the illumination apparatus 110, body 120, and/or cannula 130 can be sterilizable and configured for multiple uses. For example, illumination apparatus 110, body 120, and/or cannula 130, can be autoclavable and/or otherwise sterilizable.

Two or more optical fibers or optical fiber devices can be disposed within lumen 132 of the cannula 130. Although the exemplary embodiments in the Figures illustrate one optical fiber and one optical fiber device disposed within the cannula, any suitable number of optical fibers and optical fiber devices, including three, four, or more may be implemented in an illumination device. Optical fiber 140 and optical fiber device 150 may include a core, a cladding, and a coating, and/or other layer(s). The core of optical fibers can be a cylinder of glass, plastic, silica, and/or other suitable material through which light propagates. Cladding can surround the core and confine the light within the core. The cladding can include a dielectric material with an index of refraction less than the index of refraction of the core. A coating can surround the cladding and protect the optical fiber from physical damage. As illustrated in FIG. 8, the optical fiber 140 can have a diameter 148, and the optical fiber device 150 can have a diameter 158. The diameter 148 and/or the diameter 158 can be between approximately 25 microns and approximately 300 microns, between approximately 35 microns and 200 microns, between approximately 50 microns and approximately 100 microns, including values such as 30 microns, 40 microns, 45 microns, 75 microns, and/or other suitable values, both larger and smaller.

As illustrated in FIGS. 1, 5A, 5B and 5C, optical fiber 140 can emit light 142 into the surgical field, and optical fiber device 150 can emit light 152 into the surgical field. For example, input device 180 (seen in FIGS. 2-4) receives user input to cause optical fiber 140 and/or optical fiber device 150 to selectively illuminate the eye of the patient. The field illumination profiles of light 142, 152 are different, providing enhanced visualization to a user. For example, light 142 can provide wide-field, volumetric illumination. Wide-field illumination can facilitate the user's situational awareness within the surgical field while performing various surgical maneuvers. Light 152, on the other hand, provides planar field illumination. Planar field illumination may isolate the scattered light from a single plane in a viewing path. Such planar field illumination can allow the user to see anatomy within the eye that may not be clearly visible with wide-field volumetric illumination. For example, the vitreous humor, the clear jelly that fills the posterior segment of the patient's eye, can be more clearly visualized using planar field illumination. The user can selectively utilize planar field illumination to view the vitreous humor, for example, during vitrectomy procedure. By controlling which of optical fiber 140 or optical fiber device 150 transmits light, the user can switch between wide-field volumetric illumination and planar field illumination based on the surgical tasks being performed.

Figure 6B:
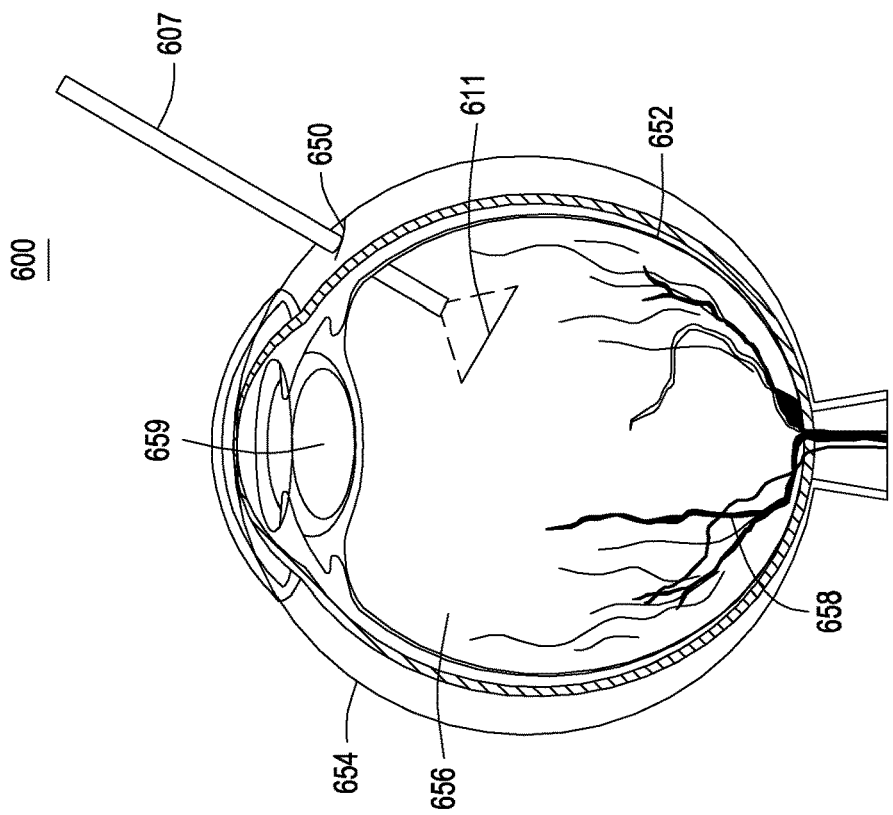
FIGS. 6A and 6B are side views of an eye with the distal portion of a cannula comprising optical fibers inserted into an eye.
Figure 6A:
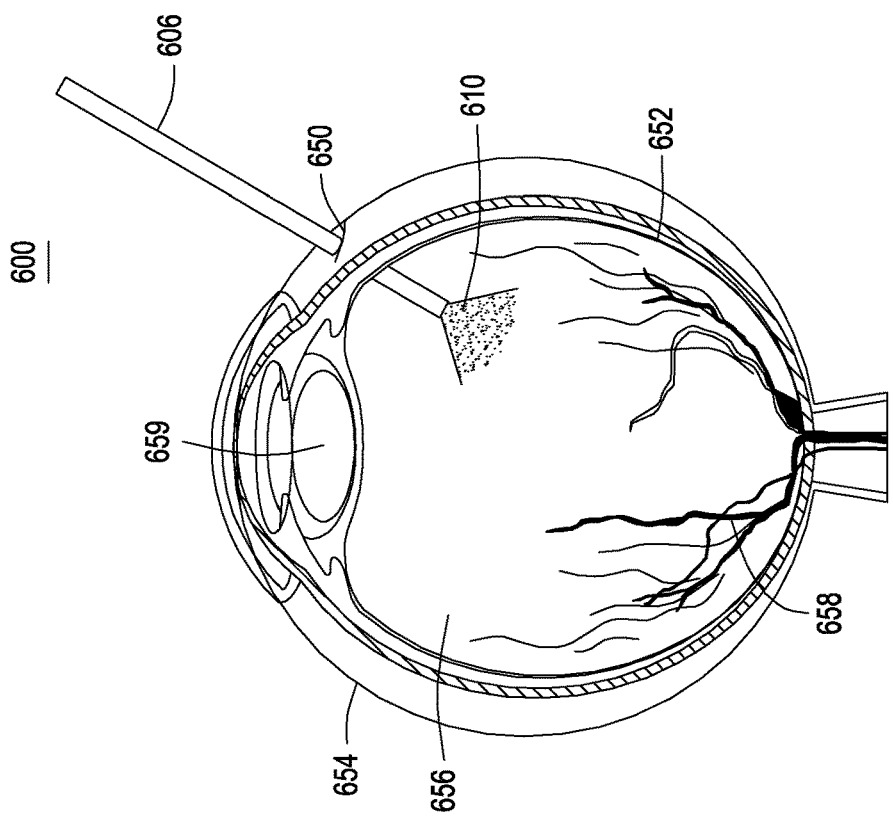

FIGS. 6A and 6B show a side view of an eye 600 with the distal portion of a cannula providing light from optical fibers inserted into an eye. Both Figures illustrate incision 650, through which cannula (606 in FIG. 6A and 607 in FIG. 6B) is inserted, retina 652, retinal blood vessels 658, vitreous body 656, cornea 654, and iris 659. FIG. 6A shows illumination from a prior art cannula 606 having an optical fiber providing wide-field volumetric illumination 610. FIG. 6B shows illumination from cannula 607 having an optical fiber device as described herein that can emit a planar light beam 611.

Figure 6C:
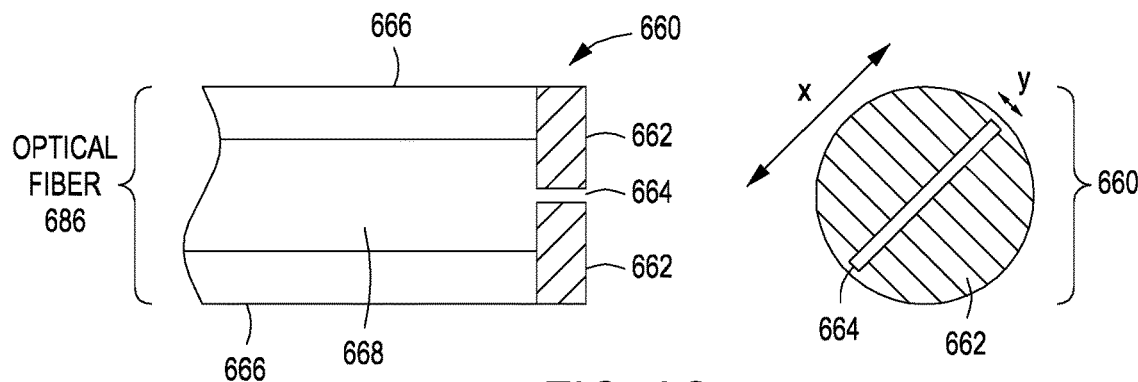
FIG. 6C illustrates an exemplary optical fiber device that provides a planar light beam using an optical slit.

FIG. 6C illustrates two views of an exemplary optical slit device 660 comprising an optical fiber device that provides a planar light beam using an optical slit 664. Optical slit device 660 comprises an optical slit 664 situated within an end cap 662. The side view of the optical slit device 660 of FIG. 6C shows optical fiber 686 comprising a core 668 encased in cladding 666. A diameter of core 668 of optical fiber 686 can be between approximately 5 microns and 125 microns, or between approximately 10 microns and 100 microns, or between approximately 20 microns and 75 microns, and/or other suitable sizes, both larger and smaller. Core 668 of optical fiber 686 can be made from a glass or plastic fiber or other suitable material through which light propagates. Cladding 666 typically includes a dielectric material with an index of refraction less than the index of refraction of the core. Thickness of cladding 666 surrounding core 668 can be between approximately 50 microns and 200 microns, or between approximately 75 microns and 150 microns, or between approximately 75 microns and 100 microns, and/or other suitable sizes, both larger and smaller. The optical slit device 660 can be fixedly coupled to optical fiber 686 via an anionic bond. Optical slit 664 can have an x-dimension (length) that typically is less than the diameter of core 668 of optical fiber 686; that is the x-dimension of optical slit 664 can be between approximately 4 microns and 124 microns, or between approximately 10 microns and 100 microns, or between approximately 20 microns and 75 microns, and/or other suitable sizes, both larger and smaller. A y-dimension (height) of optical slit 664 can be between approximately 5 microns and 100 microns, or between approximately 10 microns and 75 microns, or between approximately 20 microns and 50 microns, and/or other suitable sizes, both larger and smaller. End cap 662 can be made from, e.g., etched silicon, sputtered gold, vapor deposited platinum, laser structured glass, glass with a dielectric reflective layer, or any other suitable material.

Figure 6D:
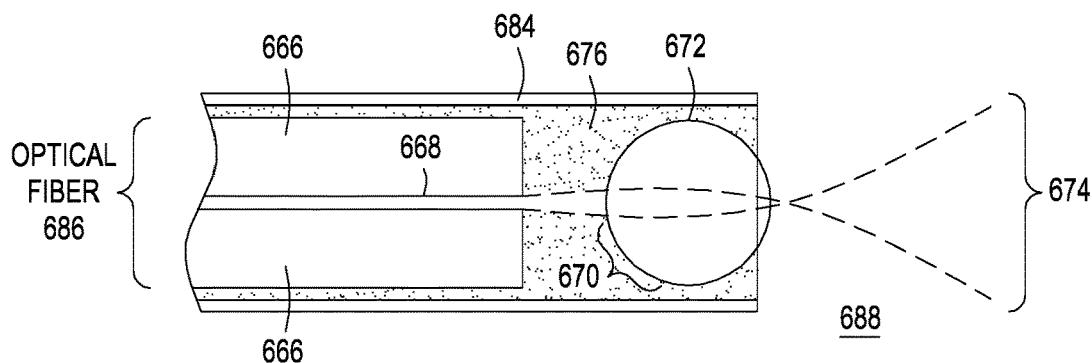
FIGS. 6D and 6E illustrate an exemplary optical fiber device that provides a planar light beam using a rod lens.
Figure 6E:
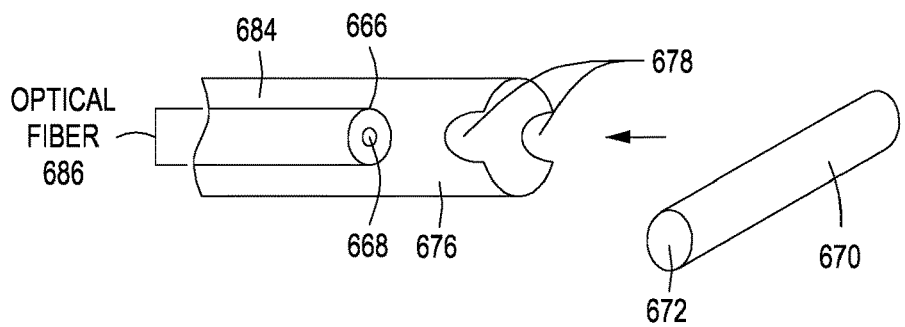

FIGS. 6D and 6E illustrate an exemplary optical fiber device that provides a planar light beam using a rod lens. FIG. 6D is a side view of an optical lens device 688 comprising an optical fiber 686 that provides a planar light beam using a rod lens 670. Optical fiber 686 is axially disposed and retained within optical lens device 688 by optical lens device housing 684, which may fully circumferentially encompass optical fiber 686. As described with reference to Figure 6C, optical fiber 686 may comprise a core 668 encased in cladding 666. A diameter of optical core 668 of optical fiber device 150 in this embodiment can be between approximately 5 microns and 75 microns, or between approximately 10 microns and 65 microns, or between approximately 20 microns and 50 microns, and/or other suitable sizes, both larger and smaller. Thickness of cladding 666 surrounding core 668 can be between approximately 50 microns and 200 microns, or between approximately 725 microns and 150 microns, or between approximately 750 microns and 100 microns, and/or other suitable sizes, both larger and smaller. In this exemplary embodiment, core 668 is made from a glass fiber such as SMF-28® Ultra Optical Fiber (Corning, Inc.) or other suitable material through which light propagates. In addition to optical fiber 686 and optical lens device housing 684, optical lens device 688 comprises rod lens 670, perpendicularly disposed of a distal end of optic fiber 150. Rod lens 670 has a rod shape, with rod lens ends 672, where rod lens 670 has a diameter that can be between approximately 75 microns and 150 microns, or between approximately 100 microns and 125 microns, and/or other suitable sizes, both larger and smaller. Rod lens 670 may be a sapphire lens or any other biocompatible, transparent material with an index of refraction considerably larger than water, such as, e.g., polycarbonate, various types of glass, or cubic zirconia, and is disposed and may be retained within optical lens device housing 684 using a suitable adhesive such as, e.g., two part epoxy or light-curable epoxy. Additionally seen in FIG. 6D is light path 674 comprising a planar light beam shaped by the rod lens.

FIG. 6E is an exemplary perspective view of the optical lens device 688 seen in FIG. 6D. FIG. 6E illustrates optical fiber 686 axially disposed within optical lens device housing 684. Optical lens device housing 684 comprises two notches 678 into which rod lens 670 is disposed. Optical lens device 688 may be formed, in some embodiments, by constructing the optical lens device housing 684 and optical fiber 686 combination, creating notches in a distal end of the optical lens device housing 684, filling the distal end of the optical lens device housing 684 with adhesive, and positioning the rod lens within the notches. Ends 672 of rod lens 670 can then be grinded or otherwise trimmed to be flush with the outer surface of optical lens device housing 684.

Figure 6F:
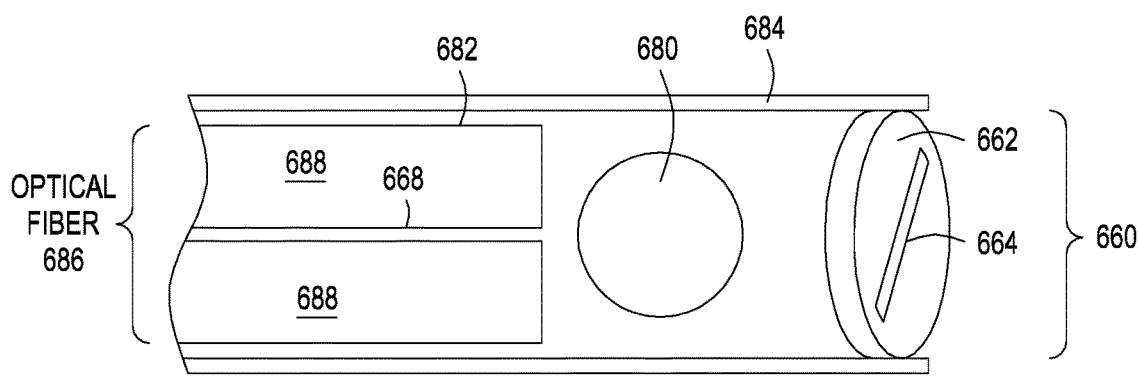
FIG. 6F illustrates an exemplary optical fiber device that provides a planar light beam using a combination of an optical slit and a ball lens.

FIG. 6F illustrates an exemplary optical fiber device 690 that provides a planar light beam using a combination of an optical slit and a ball lens. Optical fiber device 690 in this embodiment comprises optical lens device housing 684, comprising optical fiber 686 having core 668 surrounded by cladding 666, ball lens 680 and optical sit device 660. As in previously described exemplary embodiments, the diameter of optical core 668 of optical fiber 686 can be between approximately 5 microns and 125 microns, or between approximately 10 microns and 100 microns, or between approximately 20 microns and 75 microns, and/or other suitable sizes, both larger and smaller. Core 668 of optical fiber 686 can be made from a glass or plastic fiber or other suitable material. Thickness of cladding 666 surrounding core 668 can be between approximately 50 microns and 200 microns, or between approximately 75 microns and 150 microns, or between approximately 75 microns and 100 microns, and/or other suitable sizes, both larger and smaller. The optical slit device 660 can be fixedly coupled to optical fiber 686 via an anionic bond. Optical slit 664 can have an x-dimension (length) that typically is less than the diameter of core 668 of optical fiber 686; that is the x-dimension of optical slit 664 can be between approximately 4 microns and 124 microns, or between approximately 10 microns and 100 microns, or between approximately 20 microns and 75 microns, and/or other suitable sizes, both larger and smaller. A y-dimension (height) of optical slit 664 can be between approximately 5 microns and 100 microns, or between approximately 10 microns and 75 microns, or between approximately 20 microns and 50 microns, and/or other suitable sizes, both larger and smaller. Ball lens 680 may be a sapphire lens comprising a spherical shape, and can be between approximately 100 microns and 500 microns, or between approximately 150 microns and 450 microns, or between approximately 200 microns and 350 microns in diameter, and/or other suitable sizes, both larger and smaller. The ball lens 680 in this exemplary embodiment disperses light from optical fiber 686, where the light is then focused by the optical slit 664 into a plane. In addition to the rod and ball lenses exemplified herein, other lenses, singly or in combination, may be used in the optical fiber devices to provide light with a planar illumination profile.

Referring again to FIGS. 5A 5B, 5C, 7 and 8, optical fiber 140 and optical fiber device 150 can be coupled to the cannula 130. As illustrated in FIG. 8, for example, optical fiber 140 and optical fiber device 150 are coupled an inner wall 131 of cannula 130. Optical fiber 140 and/or optical fiber device 150 can be fixedly coupled such that optical fiber 140 and optical fiber device 150 do not move with respect to cannula 130. Any suitable coupling, including an adhesive, a mechanical structure, and/or combinations thereof, can be implemented. As seen in FIGS. 5A and 5B, distal portion 146 of optical fiber 140 and distal portion 156 of optical fiber device 150 can be aligned with the distal portion 136 of cannula 130. For example, distal end 147 of optical fiber 140 and/or distal end 157 of optical fiber device 150 can be laterally aligned with distal end 137 of cannula 130. In that regard, the distal ends 137, 147, 157 can be coplanar. Optical fiber 140 and optical fiber device 150 can be positioned relative to cannula 130 such that cannula 130 impedes none of the light 142, 152.

Alternatively and referring to FIG. 5C, optical fiber 140 and/or optical fiber device 150 can be movably coupled to cannula 130. For example, optical fiber 140 and optical fiber device 150 can be translatable with respect to cannula 130. Any suitable coupling, such as a mechanical structure, can be implemented. Optical fiber 140 and optical fiber device 150 may be configured to selectively move laterally with respect to cannula 130 in directions 502, 504. For example, the user can provide input at the input device 180 (see FIGS. 2-4), such as the controls 810 or 812 (see FIG. 7), a surgical footswitch (not shown), or controls integrated in a surgical console 160 (see FIG. 1). Input device 180 is in communication with illumination device 110 such that optical fiber 140 and optical fiber device 150 are translated laterally in the directions 502, 504 in response to the user input. Thus, distal ends 147, 157 of optical fiber 140 and optical fiber device 150, respectively, can be positioned proximal of, distal of, or aligned with distal end 137 of cannula 130. The user can control the angular divergence of light 142 or the plane of illumination of light 152 by selectively translating optical fiber 140 and optical fiber device 150. For example, as illustrated, optical fiber device 150 can be translated laterally in direction 502, where distal end 137 of cannula 130 is thus positioned distally beyond distal end 157 of optical fiber device 150. As a result, light 152 can be positioned to focus light on different planar fields (e.g., 152a, 152b, or 152c) than if distal end 157 of optical fiber device 150 and distal end 137 of cannula 130 were aligned.

Optical fiber 140 and optical fiber device 150 thus are coupled to one or more light sources configured to output light to illuminate the surgical field. Referring to FIG. 2, optical fiber 140 and optical fiber device 150 can be coupled to a light source 210. The light source 210 can include ports 164, 166. Light output by light source 210 can be selectively directed to port 164 and/or port 166 via, e.g., a beam director. For example, the user can select via, e.g., input device 180, which of optical fiber 140 or optical fiber device 150 transmits light to the surgical field based on which of ports 164, 166 light source 210 provides light to. As an alternative and referring to FIG. 3, optical fiber device 150 can be coupled to light source 210, and optical fiber 140 can be coupled to light source 240. Light source 240 can direct light to a port 244, and light source 210 can direct light to the port 166. In such an embodiment the user may select which of optical fiber 140 and/or optical fiber device 150 transmits light to the surgical field based on user input received by input device 180 selecting which of light sources 210, 240 outputs light.

Light source 210 and/or light source 240 can include a laser source, such as a supercontinuum laser source, an incandescent light bulb, a halogen light bulb, a metal halide light bulb, a xenon light bulb, a mercury vapor light bulb, a light emitting diode (LED), other suitable sources, and/or combinations thereof. For example, light sources 210, 240 as described herein can be configured to output bright, broadband, and/or white light to the surgical field. Light sources 210, 240 can be configured to output any suitable wavelength(s) of light, such as a visible light, infrared light, ultraviolet (UV) light, etc. Light sources 210, 240 can be in communication with optics, such as lenses, mirrors, filters, and/or gratings (such as an optical slit), configured to vary the focus or wavelength of light.

Referring to FIGS. 4 and 7, the ophthalmic illumination system 100 can include an optical relay 400. Optical relay 400 can be positioned between light source 210 and illumination apparatus 110. A single optical fiber 402 can be coupled to light source 210 and optical relay 400 and extend between light source 210 and optical relay 400, transmitting light from light source 210 to optical relay 400. Optical fiber 140 and optical fiber device 150 can be coupled to the optical relay 400, where optical relay 400 can be configured to direct the light transmitted by optical fiber 402 to optical fiber 140 or optical fiber device 150. For example, the user can provide input at input device 180 such as controls 810 or 812 of the illumination apparatus 110, the surgical footswitch (not shown), or the controls integrated in the surgical console 160. The input device 180 thus would be in communication with optical relay 400, such as via computing device 200. Optical relay 400 can include a switch, a butt coupler, any suitable combination of optics, such as lenses, such as a gradient index (GRIN) lens, rod or ball lens, mirrors, optical slits, filters, and/or gratings, other suitable components, and/or combinations thereof. For example, the switch of optical relay 400 can be configured to selectively direct light to optical fiber 140 and/or optical fiber device 150 in response to user input. Implementing optical fiber 402 and optical relay 400 can advantageously focus light on different planes within the eye by optical fiber device 150.

Optical relay 400 can be positioned at any location between light source 210 and illumination device 100, including within optical fiber 402 and cannula 130 of illumination apparatus 110. As illustrated in FIG. 7, optical relay 400 can be positioned within body 120 of illumination apparatus 110. Optical fiber 402 can extend between light source 210 and body 120, and optical fiber 140 and optical fiber device 150 can extend between body 120 and cannula 130.

Referring to FIGS. 7 and 8, illumination apparatus 110 can include a deflection mechanism 800 configured to selectively bend, angle, bow, curve, and/or otherwise cause cannula 130 to obtain a non-linear shape. For example, the cannula 130 can be articulated or otherwise made of up two or more individual components. The multiple, individual components of the cannula can allow for the cannula to be at least temporarily deflected such that the light output by optical fiber 140 and optical fiber device 150 can be directed to any desired anatomy within the surgical field, including anatomy not positioned in front of distal portion 136 of cannula 130. For example, cannula 130 can be selectively deflected to illuminate the periphery of the patient's eye. The distal portion 136, the proximal portion 137, and/or any portion of cannula 130 between the distal and proximal portions 136, 137 can be articulated and/or deflected. The deflection mechanism 800 can be coupled to one, two, three, four, or more pull wires 802 disposed within cannula 130. Deflection mechanism 800 can include any suitable components configured to actuate the one or more pull wires 802 to selectively deflect cannula 130. Cannula 130 can be biased to return to a linear configuration when pull wires 802 no longer act on cannula 130. Deflection mechanism 800 can be coupled to and/or disposed within body 120. The user can control deflection mechanism 800, including the direction and extent of the deflection of cannula 130, using the controls 810, 812 of body 120.

Referring to FIGS. 2, 3, 4, 7, and 8, the ophthalmic illumination system 100 can include a therapeutic light source 220. Therapeutic light source 220 can be part of a therapeutic beam delivery system, such as a laser beam delivery system, a photocoagulation system, a photodynamic therapy system, a retinal laser treatment system, or other appropriate system. An optical fiber 222 can be coupled to a port 224 of therapeutic light source 220. Optical fiber 222 can transmit the therapeutic beam to the surgical field as directed by the surgeon.

The ophthalmic illumination system 100 can also in some embodiments include an endoscopy subsystem 230. The endoscopy subsystem 230 can be configured to image the surgical field. For example, a user can visualize the surgical field during the surgical procedure using a surgical microscope. The endoscopy subsystem 230 can be used to visualize the area of the eye being operated on when the user cannot view that area through the lens with the surgical microscope. For example, the lens may be cloudy or the optical path of the surgical microscope may be blocked. The user can also use the endoscopy subsystem 230 to see the periphery of the eye, which may be not visible with the surgical microscope. An endoscopic fiber bundle 232 can be coupled to the endoscopy subsystem 230 at a port 234. The endoscopic fiber bundle 232 can include multiple individual fibers 236. The endoscopic fiber bundle 232 can receive and transmit light reflected from the surgical field, and can generate images based on the received light. The images can be output to a display device 168 in communication with the endoscopy subsystem 230.

Optical fiber 222 associated with the therapeutic light source 220 and the endoscopic fiber bundle 232 associated with the endoscopy subsystem 230 can be coupled to the illumination device 110. For example, optical fiber 222 and endoscopic fiber bundle 232 can be coupled to and disposed within cannula 130. Any suitable fixed or movable coupling, including an adhesive, a mechanical structure, and/or combinations thereof, can be implemented. The diameter 148 of optical fiber 140, the diameter 158 of optical fiber device 150, the diameter of the optical fiber 222, and the diameter of the endoscopic fiber bundle 232 can allow for multiple optical fibers to be positioned within the diameter 134 of cannula 130. Implementing multiple optical fibers within the single illumination device 110 and cannula 130 can advantageously decrease the number of components the user interacts with and that enter the eye during the surgical procedure. As illustrated in FIG. 7, a conduit 820, including include optical fiber 402, optical fiber 222, and endoscopic fiber bundle 232, can extend between the illumination device 110 and a surgical console 160 (not shown in FIG. 7). Conduit 820 can also include optical fiber 140 and optical fiber device 150. The user can control delivery of the therapeutic light source 220 and/or the endoscopy subsystem 230 using input device 180, such as controls 810 or 812 of illumination apparatus 110, the surgical footswitch (not shown), and/or the controls integrated in the surgical console 160.

Referring to FIGS. 1, 2, 3, and 4, light source 210, light source 240, therapeutic light source 220, endoscopy subsystem 230, a probe subsystem 172, and a computing device 200 can be integrated into surgical console 160. The surgeon can utilize the surgical console 160 to control one or more parameters associated with the ophthalmic surgical procedure. One or more components of the surgical console 110 can be coupled to and/or disposed within a base housing 162 illustrated in FIG. 1. Base housing 162 can be mobile such that it can be positioned proximate to the patient during the ophthalmic surgical procedure. Base housing 162 can include pneumatic, optical, fluid, and/or electrical supply lines facilitating communication between components of the ophthalmic illumination system 100.

Computing device 200 can be in communication with input device 180, light source 210, light source 240, therapeutic light source 220, endoscopy subsystem 230, probe subsystem 172, and display device 168. Computing device 200 can be configured transmit control signals to and/or receive input or status signals from the components of ophthalmic illumination system 100. For example, computing device 200 can control activation and deactivation of light sources 210, 240, transmission of light to ports 164, 166, 244, 246, transmission of light by optical fiber 140 and optical fiber device 150, as well as the focus, intensity, wavelength, and/or other characteristics of light output by light sources 210, 240. In that regard, light sources 210, 240 can be in electrical communication with the computing device 200. Computing device 200 may include a processing circuit having a processor 202 and a memory 204. Processor 202 can execute computer instructions, such as those stored on the memory 204, to control various components of the ophthalmic illumination system 100. Processor 202 can be a targeted device controller and/or a microprocessor. Memory 204, such as semiconductor memory, RAM, FRAM, or flash memory, can interface with processor 202. As such, processor 202 can write to and read from memory 204, and perform other common functions associated with managing memory 204. The processing circuit of computing device 202 can be an integrated circuit with power, input, and output pins capable of performing logic functions.

Computing device 200 can output display data to the display device 168 to display data relating to system operation and performance during an ophthalmic surgical procedure. Display device 168 can also display images generated by the endoscopy subsystem 230. Display device 168 can be a standalone device, integrated into surgical console 160, and/or in communication with the surgical microscope. For example, the images generated by the endoscopy subsystem 230 can be provided to the user as graphical overlay in a field of view of the surgical microscope.

Probe subsystem 172 also can be in electrical communication with the computing device 200. Probe subsystem 172 can include various components facilitating operation of probe 170. The user can utilize probe 170 within the surgical field to perform one or more surgical maneuvers. For example, probe 170 can be a cutting probe, a vitrectomy probe, a phacoemulsification probe, a laser probe, an ablation probe, a vacuum probe, a flushing probe, scissors, forceps, an aspiration device, and/or other suitable surgical device. Probe 170 can be in mechanical, electrical, pneumatic, fluid, and/or other suitable communication with probe subsystem 172.

Input device 180 can be in communication with computing device 200. Input device 180 can be configured to allow the user to control ophthalmic illumination system 100, including which of optical fiber 140 and optical fiber device 150 transmit light to illuminate the surgical field, selectively moving optical fiber 140 and optical fiber device 150, activating/deactivating light sources 210, 240, and/or other features described herein. Input device 180 can comprise any of a variety of ON/OFF switches, buttons, toggles, wheels, digital controls, touchscreen controls, or other user interface components. Input device 180 can be integrally disposed on the surgical console 160 and/or the illumination apparatus 110. For example, input device 180 can be one or more controls 810, 820 of the illumination apparatus 110, or input device 162 can be a distinct component, such as, by way of non-limiting example, a surgical footswitch, a remote control device, a touchscreen control device, and/or another computing device. Ophthalmic illumination system 100 can include multiple input devices 180. Input device 180 can generate and transmit input signals based on the received user input, where computing device 200 can receive and process the input signal. Computing device 200 can then generate and transmit control signals to light source 210, light source 240, therapeutic light source 220, endoscopy subsystem 230, probe subsystem 172, and display device 168.

Embodiments as described herein provide exemplary devices, systems, and methods of illuminating the surgical field using light with different illumination field profiles, including a light that provides planar field illumination. Multiple optical fibers sized and shaped to output the light with the different illumination field profiles can be implemented in a single illumination device. The preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims. In the claims that follow, unless the term "means" is used, none of the features or elements recited therein should be construed as means-plus-function limitations pursuant to 35 U.S.C. §112, ¶6.

The invention claimed is:

1. An ophthalmic illumination apparatus, comprising:
a body sized and shaped for grasping by a user;
a cannula coupled to the body, wherein the cannula comprises a distal end configured to be positioned within an eye of a patient;
an optical fiber disposed within the cannula, wherein the optical fiber is configured to emit light into a surgical field having a volumetric illumination profile, wherein the light having the volumetric illumination profile is emitted out of a distal end of the optical fiber; and
an optical fiber device disposed within the cannula, wherein the optical fiber device is configured to emit light into the surgical field having a planar illumination profile, wherein the light having the planar illumination profile is emitted out of a distal end of the optical fiber device;
wherein the distal end of the optical fiber emitting the light having the volumetric illumination profile and the distal end of the optical fiber device emitting the light having the planar illumination profile are laterally aligned with the distal end of the cannula such that the distal end of the optical fiber, the distal end of the optical fiber device, and the distal end of the cannula are coplanar;
wherein the ophthalmic illumination apparatus is configured to selectively emit the volumetric illumination profile from the optical fiber into the surgical field or the planar illumination profile from the optical fiber device into the surgical field based on a user input designating which of the volumetric or planar profile is desired.

2. The apparatus of claim 1, wherein:
the optical fiber device comprises one of an optical slit, a rod lens, or a ball lens.

3. The apparatus of claim 1, wherein:
at least one of the optical fiber or the optical fiber device is translatable with respect to the cannula.

4. The apparatus of claim 1, further comprising:
an input device configured to receive the user input to cause one and only one of the optical fiber or the optical fiber device to selectively illuminate the eye of the patient until a different user input is received designating a different one of the optical fiber or the optical fiber device is to be used to illuminate the eye.

5. The apparatus of claim 4, further comprising:
a light source coupled to the optical fiber and the optical fiber device, and configured to output light to selectively illuminate the eye of the patient via the optical fiber or the optical fiber device.

6. The apparatus of claim 5, further comprising:
an optical relay disposed between the light source and the cannula, wherein the optical relay is configured to selectively direct the light output by the light source to one of the optical fiber or the optical fiber device in response to the user input.

7. The apparatus of claim 6, wherein:
the optical relay is disposed within the body.

8. The apparatus of claim 4, further comprising:
a first light source coupled to the optical fiber; and
a second light source coupled to the optical fiber device, wherein the first and second light sources are configured to selectively output light to illuminate the eye of the patient in response to the user input.

9. The apparatus of claim 1, further comprising:
a third optical fiber disposed within the cannula, wherein the third optical fiber is coupled to a therapeutic light source and configured to transmit a therapeutic light beam into the eye of the patient.

10. The apparatus of claim 1, further comprising:
an endoscopic fiber bundle disposed within the cannula and configured to visualize the eye the patient.

11. The apparatus of claim 1, further comprising:
a deflection mechanism coupled to the cannula and configured to selectively bend the cannula.

12. The apparatus of claim 1, further comprising:
an optical fiber device housing;
one or more of an optical slit device, a rod lens, and a ball lens coupled to the optical fiber device housing.

13. The apparatus of claim 12, comprising:
the rod lens coupled to a distal end of the optical fiber device housing.

14. The apparatus of claim 12, comprising:
the ball lens disposed within a distal end of the optical fiber device housing; and
the optical slit device comprising an optical slit disposed within an optical end cap coupled to the distal end of the optical fiber device housing.

15. The apparatus of claim 12, comprising:
the ball lens disposed within a distal end of the optical fiber device housing; and
the rod lens coupled to the distal end of the optical fiber device housing.

16. An ophthalmic illumination apparatus, comprising:
a body sized and shaped for grasping by a user;
a cannula coupled to the body and configured to be positioned within an eye of a patient;
an optical fiber disposed within the cannula, wherein the optical fiber is configured to emit light into a surgical field having a volumetric illumination profile; and
an optical fiber device disposed within the cannula, wherein the optical fiber device is configured to emit light into the surgical field having a planar illumination profile;
wherein the ophthalmic illumination apparatus is configured to selectively emit the volumetric illumination profile from the optical fiber into the surgical field or the planar illumination profile from the optical fiber device into the surgical field based on a user input designating which of the volumetric or planar profile is desired;
wherein the ophthalmic illumination apparatus further comprises:
an optical fiber device housing;
one or more of an optical slit device, a rod lens, and a ball lens coupled to the optical fiber device housing;
the optical slit device comprising an optical slit disposed within an optical end cap coupled to a distal end of the optical fiber device housing.

* * * * *